(12) United States Patent
Markowiecki (10) Patent No.: US 6,350,258 B1
(45) Date of Patent: Feb. 26, 2002

(54) SANITARY PAD

(76) Inventor: Nora Markowiecki, 1 Tzadik Gimel Banot Street, Flat 4, Rishon Lezion (IL)

( * ) Notice: Subject to any disclaimer, the term of this patent is extended or adjusted under 35 U.S.C. 154(b) by 0 days.

(21) Appl. No.: 09/523,814

(22) Filed: Mar. 13, 2000

(51) Int. Cl.[7] .......................... A61F 13/15; A61F 13/20; A61F 13/24
(52) U.S. Cl. .......................... 604/385.201; 604/385.01; 604/385.03; 604/385.05; 604/385.14; 604/386; 604/387
(58) Field of Search .................. 604/385.01, 385.03, 604/385.05, 385.14, 386, 387, 385.201, 358

(56) References Cited

U.S. PATENT DOCUMENTS

| | | | |
|---|---|---|---|
| RE33,351 E | * | 9/1990 | Papajohn .................... 604/387 |
| 5,484,429 A | | 1/1996 | Vukos et al. ............. 604/385.1 |
| 5,683,373 A | | 11/1997 | Darby ..................... 604/385.1 |
| 5,713,886 A | | 2/1998 | Sturino ........................ 604/390 |
| 6,114,597 A | * | 9/2000 | Romare ....................... 604/378 |

* cited by examiner

*Primary Examiner*—John G. Weiss
*Assistant Examiner*—Michael Bogart
(74) *Attorney, Agent, or Firm*—Merchant & Gould PC (57) ABSTRACT

A sanitary pad including a wide portion, a narrow portion connected to the wide portion, defining two lateral notches dividing between the wide portion and the narrow portion. At least two fold lines are preformed on the narrow portion and inwardly emanate from the two lateral notches and curve downwardly away from the wide portion toward the longitudinal median of the narrow portion. In a preferable embodiment the at least two fold lines include a lower pair of fold lines preformed on the lower surface of the narrow portion and an upper pair of fold lines preformed on the upper surface of the narrow portion. The pad may also feature a traverse fold line preformed across the wide portion between the notches. In another preferable embodiment the upper part of the sides of the narrow portion overlap under the lower part of the sides of the wide portion.

34 Claims, 7 Drawing Sheets

SANITARY PAD

FIELD OF THE INVENTION

The present invention relates to the field of female sanitary pads designed to absorb feminine menstrual fluids and other body secretions, in general, and to sanitary pads attachable to undergarments in particular.

BACKGROUND OF THE INVENTION

Napkins, panty liners and sanitary pads are external protection devices designed to absorb menses and other secreted fluids, while preventing external leakage, without requiring positioning within the vagina. Some of these devices include adhesive strips, which serve to secure the device to an undergarment, primarily to the crotch of the undergarment. Various designs of such devices have been implemented in the prior art.

For example U.S. Pat. No. 5,484,429 issued to Vukos, et al. and entitled "Interlabial Sanitary Pad", is directed to a pad which absorbs and accumulates the fluids. The pad includes a pick up module adapted to fit in or adjacent to a vaginal opening, and a capacity module adapted to be positioned remote from the vaginal opening. The height dimension of the pick up module is greater than the height dimension of the capacity module. Both modules contain longitudinally oriented absorbent or wicking fibers, capable of carrying fluids from the pick up module to the capacity module. The flowing fluids progressively accumulate in the capacity module, whose crotch consequently inflates.

U.S. Pat. No. 5,713,886 issued to Sturino and entitled "Panty Liner", is directed to a sanitary napkin or panty liner, especially for use with an undergarment having a narrowed crotch portion. The napkin comprises an elongated absorbent body having a first, elongated, portion and a second, wider, portion. The opposed sides of the second portion flare from the sides of the first portion and thus the second portion is of a generally triangular outline. The first portion includes one lateral flap capable of being partially folded around the strap section of the undergarment. The second portion includes a pair of lateral flaps capable of being partially folded around the narrowed crotch of an undergarment. Adhesive strips are secured to the flaps and the elongated body for attachment to the undergarment.

U.S. Pat. No. 5,683,373 issued to Darby and entitled "Sanitary Napkin Shaped for Use With a Thong Garment", is directed to a sanitary pad configured to fit within the confines of a thong shaped garment having a narrow elongated crotch portion. The configuration of the pad is overall V-shaped in plan view and bulbed at its top end, while tapering therefrom longitudinally to a midportion. From there, the pad longitudinally narrows in an elongated lower end portion having a substantially uniform width, less than the width of the narrow elongated crotch portion of the thong shaped garment.

SUMMARY OF THE PRESENT INVENTION

It is an object of the present invention to provide a novel sanitary pad or napkin or panty liner, that conforms to the body confinements, adapted to fit within the confines of a commonly thong-shaped garment, substantially resistant to displacement or random creases while in use, and effective for preventing leakage of fluids secreted from the body of the user.

In accordance with the present invention, there is thus provided a sanitary pad including a wide portion, a narrow portion connected to the wide portion, defining two lateral notches dividing between the wide portion and the narrow portion, and at least two fold lines preformed on the narrow portion. The at least two fold lines inwardly emanate from the two lateral notches and curve downwardly away from the wide portion and toward the longitudinal median of the narrow portion. The at least two fold lines are preformed on the upper or lower surface of the narrow portion.

The at least two fold lines are preformed by methods such as mechanically pressing the pad along the curves of the desired fold line, joining the constituents thereof chemically, applying heat, applying a laser beam, applying an adhesive, applying mechanical vibrations, or any combination of such methods.

Either part of the thickness of the pad or its entire thickness may be joined there between to create the at least two fold lines. Optionally, a thick fold strip is formed along and on any part of the narrow portion between the at least two fold lines.

Preferably, the at least two fold lines include a lower pair of fold lines preformed on the lower surface of the narrow portion and an upper pair of fold lines preformed on the upper surface of the narrow portion. Optionally, a thick fold strip is preformed between the upper pair of fold lines and the lower pair of fold lines.

Further preferably, the sanitary pad further includes a traverse fold line preformed across the wide portion between the notches. Optionally, the traverse fold line includes an arcuate fold line, which may feature a convex side toward the wide portion. Further optionally the traverse fold line is preformed on the upper surface of the pad. Still, further optionally, either part of the thickness of the pad or its entire thickness is joined there between to create the traverse fold line. Alternatively, a thick fold strip is formed along the traverse fold line.

Preferably, the contour of the wide portion and the contour of the narrow portion converge at the notches, the contour of the wide portion emanates laterally from the notches and curves to flare toward the upper part of the wide portion, the contour of the narrow portion emanates laterally from the notches and curves to flare toward the lower part of the narrow portion. Further preferably, the contour lines of the wide portion and the narrow portion converge at the notches, and each of the at least two fold lines emanate from the notches in an uninterrupted curve continuing the contour lines of the wide portion and the narrow portion. Optionally, the at least two fold lines converge at a convergence point located on the longitudinal median of the narrow portion. Further optionally, the at least two fold lines extend along at least a substantial part of the narrow portion.

Preferably, the sanitary pad further includes a stabilizing bonding rim along the contour edges of the narrow portion and the wide portion. The stabilizing bonding may be provided by a method such as mechanically pressing, joining the constituents thereof chemically, applying heat, applying a laser beam, applying an adhesive, applying mechanical vibrations, or any combination of such methods.

Optionally, the at least two fold lines include dashed lines.

Further optionally, the upper part of the sides of the narrow portion overlap under the lower part of the sides of the wide portion.

In a preferable embodiment, the sanitary pad includes an absorbent layer, a transmitting layer, a backing sheet, and a peel away sheet, wherein adhesive layers are interleaved between the backing sheet and the peel away sheet. The absorbent layer may include a plurality of substantially parallel laminates manufactured from a fluid absorbing material, which in turn may include plastic fibers, cotton fibers, or wood pulp fibers or any of combination thereof. Preferably, the transmitting layer covers the entire upper surface of the pad, is substantially thinner than the absorbent layer, and is constructed from a cellulose material. Further preferably, the adhesive layers are manufactured from an adhesive which detachably adheres to undergarments and which is substantially inert to the human body. The peel away sheet is preferably constructed from a sheet or foil detachable from the adhesive layers without damaging the form or substance of the adhesive layers.

BRIEF DESCRIPTION OF THE DRAWINGS

The present invention will be understood and appreciated more fully from the following detailed description taken in conjunction with the drawings in which.

DETAILED DESCRIPTION OF PREFERRED EMBODIMENTS

The present invention overcomes the disadvantages of the prior art by providing a novel sanitary pad, napkin or panty liner (herein below—"pad") and a method for manufacture thereof. In its broadest aspects, after placing in an undergarment worn by the user, the pad is designed to spontaneously crease or pleat along predetermined fold-lines adapted to optimally fit the body and external female genital organ and substantially avoid displacement while in use. In addition, a section of the pad protrudes therefrom, the protrusion conforming to the pudendal fissure—namely —the slit between right and left labia majora, so that the pad incorporates partial interlabial characteristic.

Figure 1:
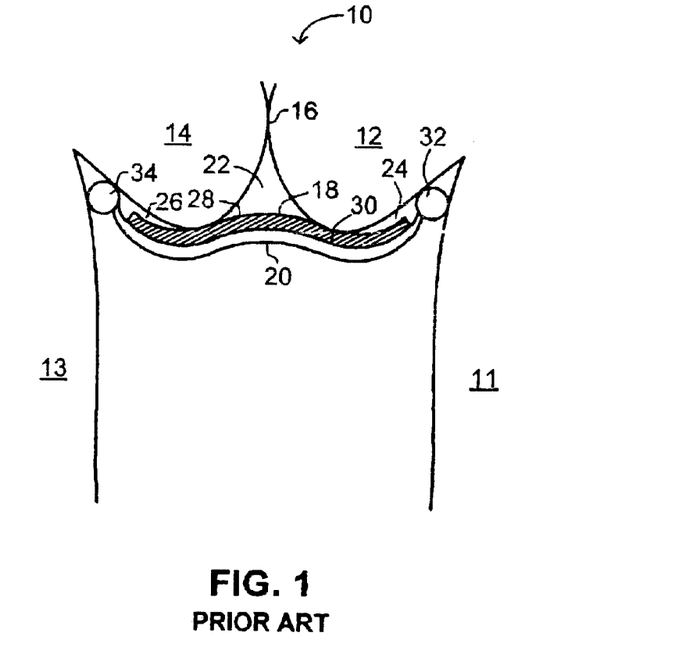
FIG. 1 is a transverse sectional view of a sanitary pad, as known in the prior art, when deployed for use on the body of a female user.

Reference is now made to FIG. 1, which is a transverse sectional view of a sanitary pad, as known in the prior art, when deployed for use on the body of a female user. A left labia majora of the female genital organ is designated by reference 12, and a right labia majora thereof is designated by reference 14. A left thigh is designated by reference 11, and a right thigh by reference 13. A pudendal fissure 16 is located between the left labia majora 12 and the right labia majora 14. It will be noted that the proportions of the body of the user may be exaggerated throughout the accompanying drawings for demonstrative purposes. A conventional sanitary pad 18 is disposed between an inner side 30 of crotch portion of an undergarment 20, and labia majora 12 and 14. The term "crotch" portion herein below refers to the frontal triangular crotch portion as well as to the bottom narrow elongated strap portion of the undergarment. A side of the conventional pad 18 facing pudendal fissure 16 is designated by reference 28. The conventional pad 18 is adhered to inner side 30 of the crotch portion of undergarment 20. A left elastic portion 32 of the undergarment 20, and a right elastic portion 34 thereof conventionally provide close contact of crotch portion of undergarment 20 with the left labia majora 12 and the right labia majora 14, adjacent to the thighs 11 and 13, correspondingly.

Secretions from a female genital organ are herein after designated by the term "fluids" or "secretions", although it may be appreciated that such fluids may include any natural excretions or exudates such as menses, uterine blood, urine, fluids generated secondary to a disease, mucous, and the like. Fluids are secreted from the pudendal fissure 16, and flow in a space 22 confined by the surfaces of the left and right labia majora 12 and 14, respectively, and the conventional sanitary pad 18.

Figure 2:
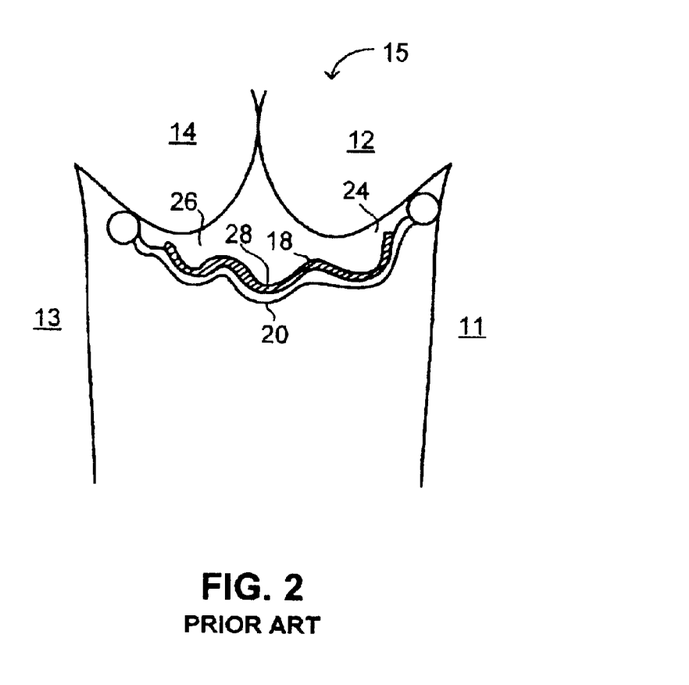
FIG. 2 is a transverse sectional view of the conventional sanitary pad of FIG. 1 after being in use for a substantial period.

Reference is now made to FIG. 2, which is a transverse sectional view of the conventional sanitary pad of FIG. 1 after being in use for a substantial period. It is noted that conventional pad 18 is subject to displacement, for example—toward the extreme right or extreme left part of left or right labia majora 12 and 14, respectively, due to movement of thighs 11 and 13 such as during walking or other physical activity. During such physical activity, the crotch portion of the undergarment 20 is creased, and along with the undergarment 20, the conventional pad 18, that is adhered to the crotch, is creased.

Such displacement or crease of pad 18 causes much discomfort to user, while parts thereof press against sensitive skin of left or right labia majora 12 and 14 or thighs 11 and 13. In addition, posterior portion 28 of conventional pad 18 moves away from fissure 16, and gaps 24 and 26 are furthermore widened as shown in FIG. 2, thus allowing increased leakage of fluids when conventional pad 18 is used. Part of the fluids are absorbed by the conventional sanitary pad 18, and the remainder can sometimes leak from gaps 24 and 26, between left and right labia majora 12 and 14, respectively, and the conventional sanitary pad 18, as shown in FIG. 1, thus wetting or contaminating the crotch portion of the undergarment 20.

It will be appreciated that when conventional pad 18 is initially positioned substantially flat below the left and right labia majora 12 and 14, respectively, it bends toward the anterior of the abdomen of the user. Thus random folds and wrinkles are imparted to the conventional pad 18, even at the first instance of use, and the conventional pad 18 folds and wrinkles substantially in a random manner. At a later stage of use, due to physical activity of the user, conventional pad 18 is displaced relative to external female genital organ, and eventually reaches a position such as shown in FIG. 2.

Figure 3:
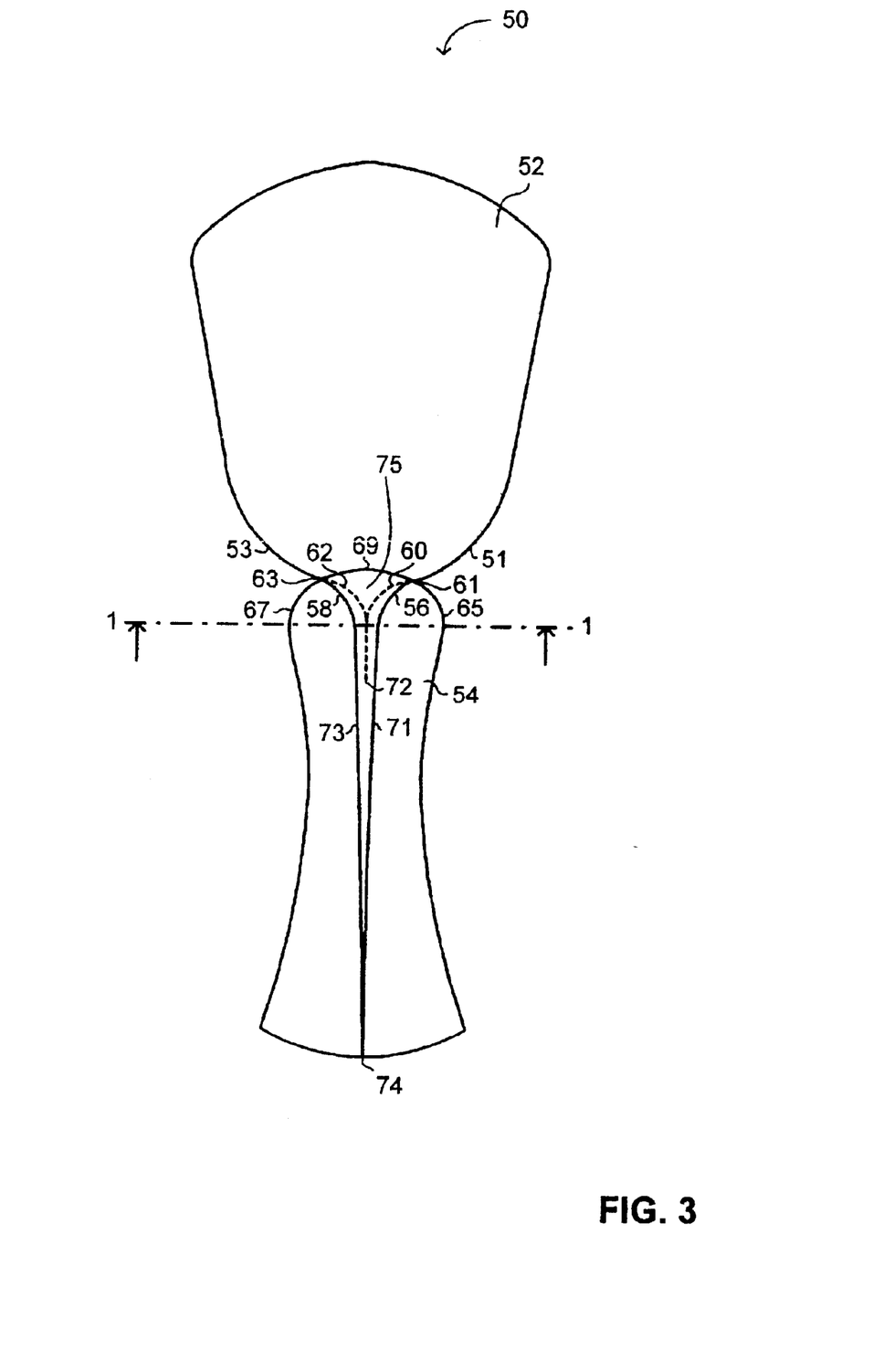
FIG. 3 is a schematic plan view of a pad, constructed and operative in accordance with a preferred embodiment of the present invention.

Reference is now made to FIG. 3, which is a schematic plan view of a pad, generally referenced 50, constructed and operative in accordance with a preferred embodiment of the present invention. The pad in FIG. 3 is shown while viewing from direction of a user. Pad 50 includes a wide portion 52, which is connected to a narrow portion 54. During use, the wide portion 52 is disposed anterior to lower abdomen (not shown), and the narrow portion 54 is disposed below the genitalia, the anus and the perineum (the region there between).

Fold lines 60 and 62 are preformed on the lower surface of narrow portion 54. Narrow portion 54 incorporates an inherent tendency to hinge on fold lines 60 and 62, rather than in regions thereof outside of fold lines 60 and 62. Narrow portion 54 deforms to the desired shape, due to fold lines 60 and 62. The curve at lines 60 or 62 operates as a "hinge" line along which the sheet folds. Such deformation is based on the tendency of semi-rigid sheets such as paper and cardboard, to deform along a curve when the sheet is bent in a direction normal to a curve. After the folding along a fold line, the pad is more rigid and inflexible to bending in a direction normal to the fold line.

Fold lines 60 and 62 may be preformed or created by methods such as mechanically pressing pad 50 along the curves of the desired fold line, joining the constituents thereof chemically, by applying heat, a laser beam, an adhesive, by applying mechanical vibration, and the like, and any combination of such methods. Either part of the thickness of pad 50, or the entire thickness thereof, may be joined there between, in order to create a fold line. Upon placement of pad 50 below the genitalia, the anus and the perineum, and the bending of narrow portion 54 as further explained herein below with reference to FIG. 5, narrow portion 54 deforms to shape which is suitable to partially fill the space 22, confined by the surfaces of the left and right labia majora 12 and 14.

Preferably, fold lines 56 and 58 may be similarly preformed on the upper surface of narrow portion 54. To further facilitate the desired deformation of narrow portion 54, fold lines 60 and 62 may be formed on the lower surface portion 54, and fold lines 56 and 58 formed on the upper surface of narrow portion 54. Alternatively, a part of narrow portion 54 may be formed as a thick fold "strip", instead of a thin fold line or a thick line, along each pair of fold lines 56 and 58, or 60 and 62, respectively. Further alternatively, narrow portion 54 may be formed as a thick fold "strip" between fold lines 56 and 60, or between 58 and 62, respectively.

To furthermore facilitate the desired deformation of narrow portion 54, a traverse fold line 69 may similarly be formed on pad 50 across a neck 75—where wide portion 52 meets narrow portion 54. It will be appreciated by those vested in the art, that the combination of traverse fold line 69, and fold lines 56 and 58 (or the combination of fold lines 56, 58, 60, and 62) facilitates deformation of narrow portion 54 to the desired shape. Fold line 69 is not necessary for operation of pad 50, because traverse fold line 69 corresponds to the spontaneous fold line that will usually occur when fold lines 56 and 58 (or 56, 58, 60, and 62) are provided. Traverse fold line 69 preferably comprises an arcuate fold line, which is preferably convex toward wide portion 52. Traverse fold line may also be preformed on the upper surface of, or lower surface of, through a part of, or the entire thickness of, pad 50, and also feature a thick fold strip.

Wide portion 52 and narrow portion 54 meet at the notched neck 75. The connection of wide portion 52 and narrow portion 54 defines two lateral notches, 61 and 63 dividing between wide portion 52 and narrow portion 54 at neck 75. Fold lines 56 and 58 (or 56, 58, 60, and 62) inwardly emanate from lateral notches 61 and 63, correspondingly, and curve downwardly away from wide portion 52 toward the longitudinal median of narrow portion 54. Each contour of sides 51 and 53 of wide portion 52, and each contour of sides 65 and 67 of narrow portion 54, curves toward neck 75, thereby the contours converge at notches 61 and 63. Hence, the side-flaps or sides 51 and 53 of wide portion 52 and sides 65 and 67 of narrow portion 54, intersect at neck 75 at intersections or notches 61 and 63. The contour of side 51 of wide portion 52 converges with the contour of side 65 of narrow portion 54 at intersection or notch 61. Similarly, the contour of side 53 of wide portion 52 converges with the contour of side 67 of narrow portion 54 at intersection or notch 63. Thus, the opposed contours of sides 51 and 53 of wide portion 52 curve to flare from neck 75 toward the upper part of wide portion 52; and the opposed contours of sides 65 and 67 of narrow portion 54 curve to flare from neck 75 toward the lower part of narrow portion 54.

Thus, the side flaps or sides 51 and 53 of wide portion 52 can fold or bend towards directions different from the bending of folding directions of the sides 65 and 67 of narrow portion 54. For example, the bending of folding of the sides 51 and 53 of wide portion 52 upwards, still allows for the bending or folding of the sides 65 and 67 of narrow portion 54 downwards, especially of those parts of sides 51, 53, 65, and 67, which extend laterally beyond the width of neck 75 (beyond intersections 61 and 63).

Fold lines 56, 58, 60, 62, and 69 each emanate from intersections 61 and 63, in an uninterrupted curve continuing the contour lines of sides 51, 53, 65, and 67. Fold lines 56, 58, 60, and 62, then curve downwards toward the bottom of narrow portion 52. Fold lines 56 and 58 converge at a convergence point 74, and fold lines 60 and 62 converge at a convergence point 72. However, it will be appreciated that the convergence points 72 and 74, can be located anywhere along the median of narrow portion 54. Preferably, convergence points 72 and 74 may be chosen to locate away from neck 75, to ensure that fold lines 56, 58, 60, and 62 extend along all or most or a substantial part of narrow portion 54. It will be noted that it is not necessary for operation of pad 50, that fold lines 56 and 58 converge at point 74 at the lower edge of narrow portion 52. Pad 50 can similarly operate if fold lines 56 and 58 end or converge at points closer to neck 75, such as points 71 and 73.

Figure 4:
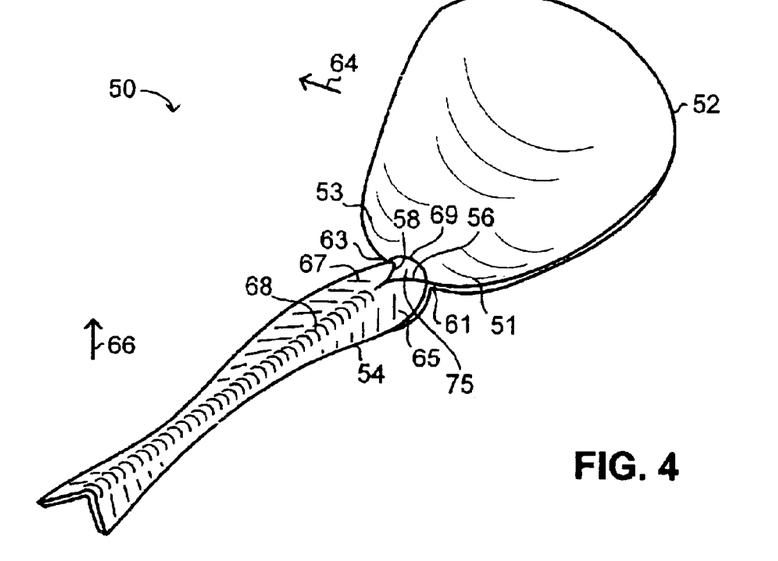
FIG. 4 is a schematic perspective view of the pad of FIG. 3, when deployed for use.

Reference is further made to FIG. 4, which is a schematic perspective view of the pad of FIG. 3, when deployed for use. When worn by the user, wide portion 52 and narrow portion 54, tilt in directions designated by arrows 64 and 66, respectively, to generally fit the curvature of the body of the user. Pad 50 folds at neck 75 along fold line 69, or a similar path, if fold line 69 is not incorporated—as explained above. Due to the fold lines 56, 58, 60, and 62 being previously present on narrow portion 54, the shape of narrow portion 54 changes from a flat surface (FIG. 3), to a bent surface (FIG. 4), characterized by an upper bend line 68, and downwardly bent flaps or side 65 and 67, to generally fit the left and right labia majora and pudendal fissure of the user. The shape of wide portion 52 slightly deforms to upwardly bent flaps or sides 51 and 53 of the surface, to generally assume the position fitting the lower abdomen of the user.

Figure 5:
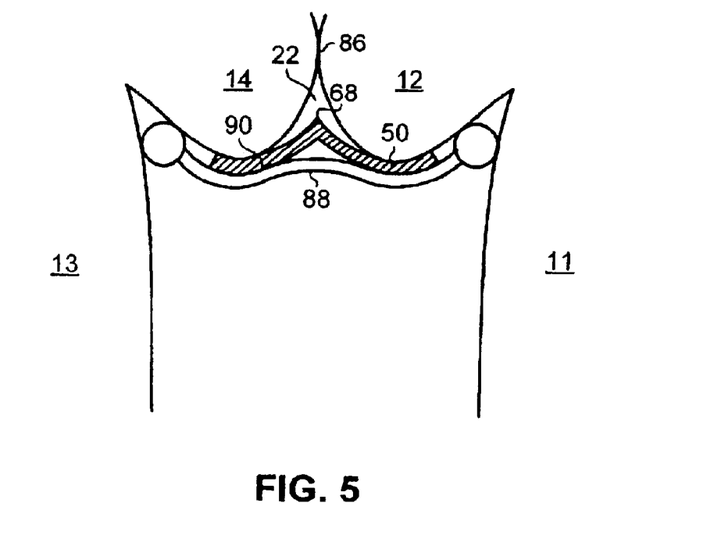
FIG. 5 is a transverse sectional view taken along broken line 1 in FIG. 3, of a line of contact of the pad shown in FIG. 3, and the body of a female user.

Reference is further made to FIG. 5, which is a transverse sectional view taken along broken line 1 in FIG. 3, of a line of contact of the pad shown in FIG. 3, and the body of a female user. When narrow portion 54 is placed below the external female genital organ, bend line 68 penetrates the space 22, confined by the surfaces of the left and right labia majora 12 and 14. A left labia majora 12 and a right labia majora 14, form a pedundal fissure 86. Narrow portion 54 of pad 50 is placed between the left and right labia majora 12 and 14, respectively, and inner side 90 of crotch portion of an undergarment 88. Bend line 68 of narrow portion 54 partially enters fissure 86, its nesting therein stabilizes pad 50, and prevents its displacement relative to the left and right labia majora 12 and 14, respectively, which is likely to occur due to physical activity of the user and movement of crotch portion of undergarment 88.

As explained above with reference to FIGS. 1 and 2, in the absence of fold lines 56, 58, 60, and 62, a conventional pad 18 is initially positioned substantially flat below the left and right labia majora 12 and 14, respectively, and bends toward the anterior of the abdomen of the user. Thus random folds and wrinkles are imparted to the conventional pad 18, even at the first instance of use, and the conventional pad 18 folds and wrinkles substantially in a random manner. At a later stage of use, due to physical activity of the user, conventional pad 18 is displaced relative to external female genital organ, and eventually reaches a position such as shown in FIG. 2. As shown in FIG. 2, gaps 24 and 26 are formed, and leakage of fluids from conventional pad 18, and contamination of crotch of the undergarment 20 is likely to occur.

On the contrary, pad 50 is positioned in fissure 86 (FIG. 5) at the first instance of use, and pad 50 does not move relative to left and right labia majora 12 and 14, respectively, even at a later stage of use, such as during physical activity of the user. At the first instance of placement of pad 50 below the external female genital organ, flaps or sides 51 and 53 of wide portion 52 (FIG. 3), tend to laterally bend in a direction above the drawing page, while flaps or sides 65 and 67 of narrow portion 54 tend to laterally bend in a direction below the drawing page. This bending is more clearly demonstrated in FIG. 4. Intersection points 61 and 63 make possible the bends in opposite directions to take place, as described above. It will be noted that the distance between intersection points 61 and 63 is designed to be substantially small, with a narrow neck 75. However, in order to provide minimal interruption to the seal between wide portion 52 and narrow portion 54, and to prevent contamination of crotch portion of undergarment 88 (FIG. 5), minimal width of neck 75 is required, and the narrowness of neck 75 should be limited.

Figure 6:
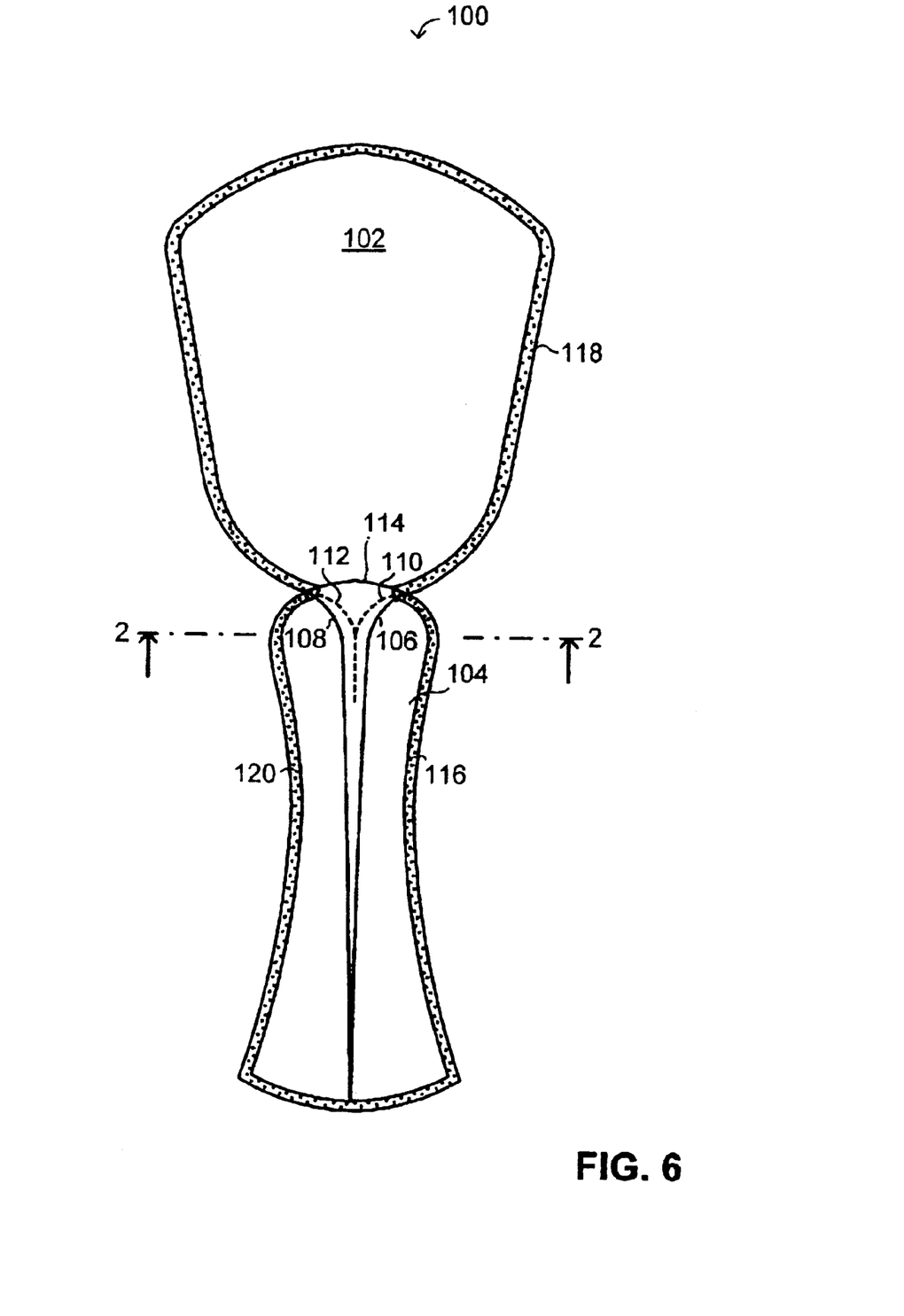
FIG. 6 is a schematic plan view of a pad, constructed and operative in accordance with another preferred embodiment of the present invention.

Reference is now made to FIG. 6, which is a schematic plan view of a pad, generally referenced 100, constructed and operative in accordance with another preferred embodiment of the present invention. Pad 100 is shown while viewing from direction of a user. Pad 100 includes a wide portion 102 and a narrow portion 104. Pad 100 further includes fold lines 106, 108, 110, 112, and 114, which correspond respectively to fold lines 56, 58, 60, 62, and 69, as described herein above in connection with FIG. 3.

Dotted sections 116 and 118 along the edges of narrow portion 104 and wide portion 102, respectively, represent a stabilizing bonding rim of pad 100 along the contour thereof. The stabilizing bonding may be provided by methods such as mechanically pressing pad 100 along the contours, joining the constituents thereof chemically, or by applying heat, a laser beam, an adhesive, or by applying mechanical vibration, and the like, and any combination of such methods.

Figure 7:
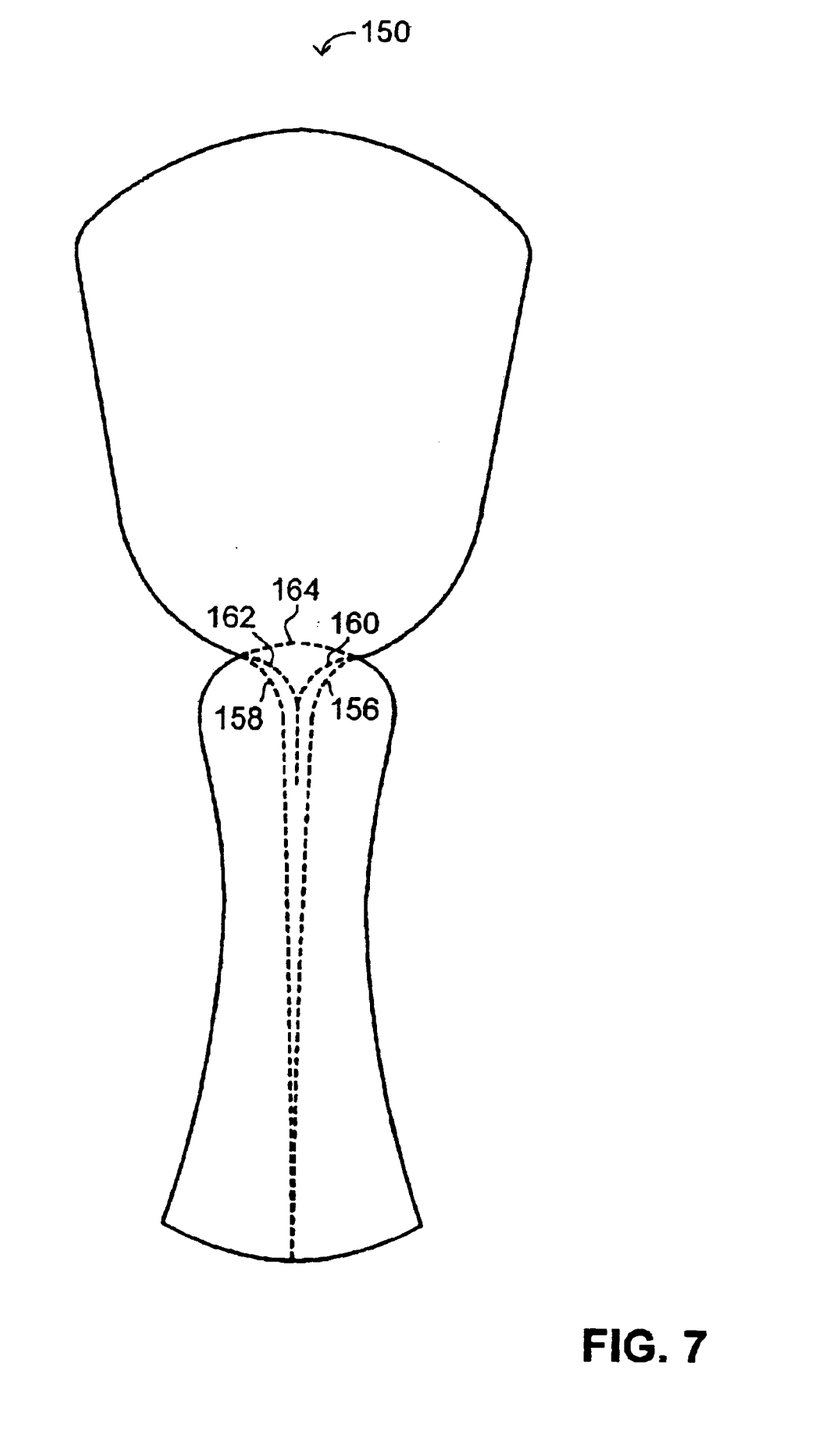
FIG. 7 is a schematic plan view of a pad, constructed and operative in accordance with a further preferred embodiment of the present invention.

Reference is further made to FIG. 7, which is a schematic plan view of a pad, generally referenced 150, constructed and operative in accordance with another preferred embodiment of the present invention. Fold lines 156, 158, 160, 162, and 164, serve the same purpose as fold lines 56, 58, 60, 62, and 69 (FIG. 3), respectively, except that the fold lines shown in FIG. 7 are dashed line and not continuous lines.

Figure 8:
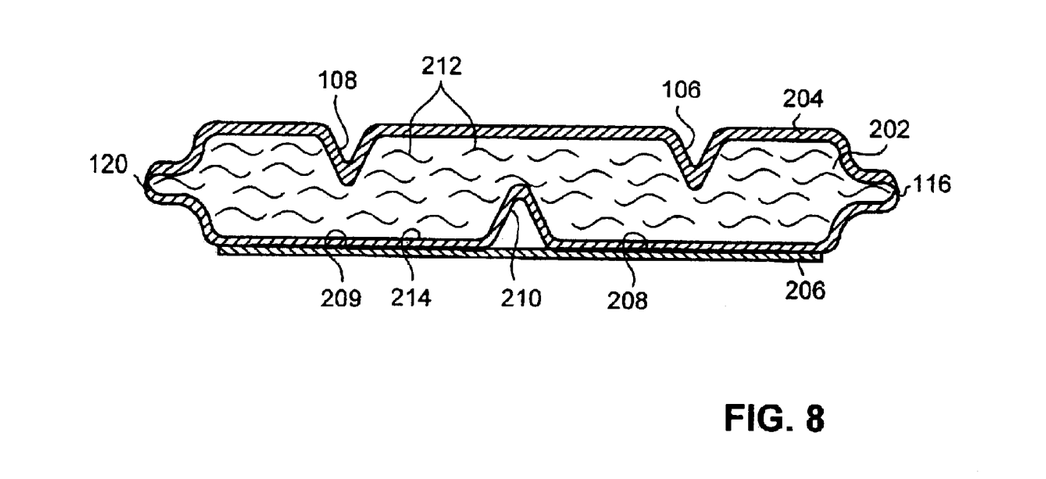
FIG. 8 is a cross-sectional enlarged view of the pad of FIG. 6, taken along broken line 2 in FIG. 6.

Reference is further made to FIG. 8 which is a cross-sectional enlarged view of the pad of FIG. 6, taken along broken line 2 in FIG. 6. Pad 100 is constructed of an absorbent layer 202, a transmitting layer 204, a backing sheet 214, and a peel away sheet 206. Adhesive layers 208 and 209 are interleaved between backing sheet 214 and peel away sheet 206. Relatively packed regions 116 and 120 of absorbent layer 202 (FIG. 8), correspond to embossed regions 116 and 120 (FIG. 6). Notches 106 and 108 (FIG. 8) correspond respectively, to fold lines 106 and 108 (FIG. 6), on the upper surface of narrow portion 104. Likewise, notch 210 (FIG. 8) corresponds to fold lines 110 and 112 (FIG. 6), converged to a single line toward the lower surface of narrow portion 104.

Absorbent layer 202 includes a plurality of substantially parallel laminates manufactured from a fluid absorbing material. Such fluid absorbing material may include plastic fibers, cotton fibers, wood pulp fibers, and the like, or combinations thereof. Absorbent layer 202 may alternatively be manufactured from individual fibers 212, or any other method known in the art.

Fibers 212 in the vicinity of fold lines 106, 108, 110, 112, and 114 are packed by methods known in the art, and as described in connection with FIG. 3, thus imparting hinge-like tendency to absorbent layer 202, relative to other regions of absorbent layer 202 not packed as such.

Transmitting layer 204 covers the entire upper surface of pad 100. Transmitting layer 204 is substantially thinner than absorbent layer 202. Transmitting layer 204 is constructed from materials such as a cellulose material known in the art, which transmits fluid to absorbent layer 202.

Adhesive layers 208 and 209 allow adhesion of pad 100 to inner side 90 (FIG. 5) of crotch of undergarment 88. Adhesive layers 208 and 209 are manufactured from an adhesive, which adheres to undergarments, as known in the art, and may be detached from the undergarment at a later line, without damaging the undergarment. Furthermore, the adhesive of adhesive layers 208 and 209 is substantially inert to the human body.

Peel away sheet 206 (FIG. 8) protects adhesive layers 208 and 209, until pad 100 is used. Peel away sheet 206 is constructed from a sheet or foil which may be detached from adhesive layers 208 and 209, without damaging the form or substance of adhesive layers 208 and 209.

Figure 9:
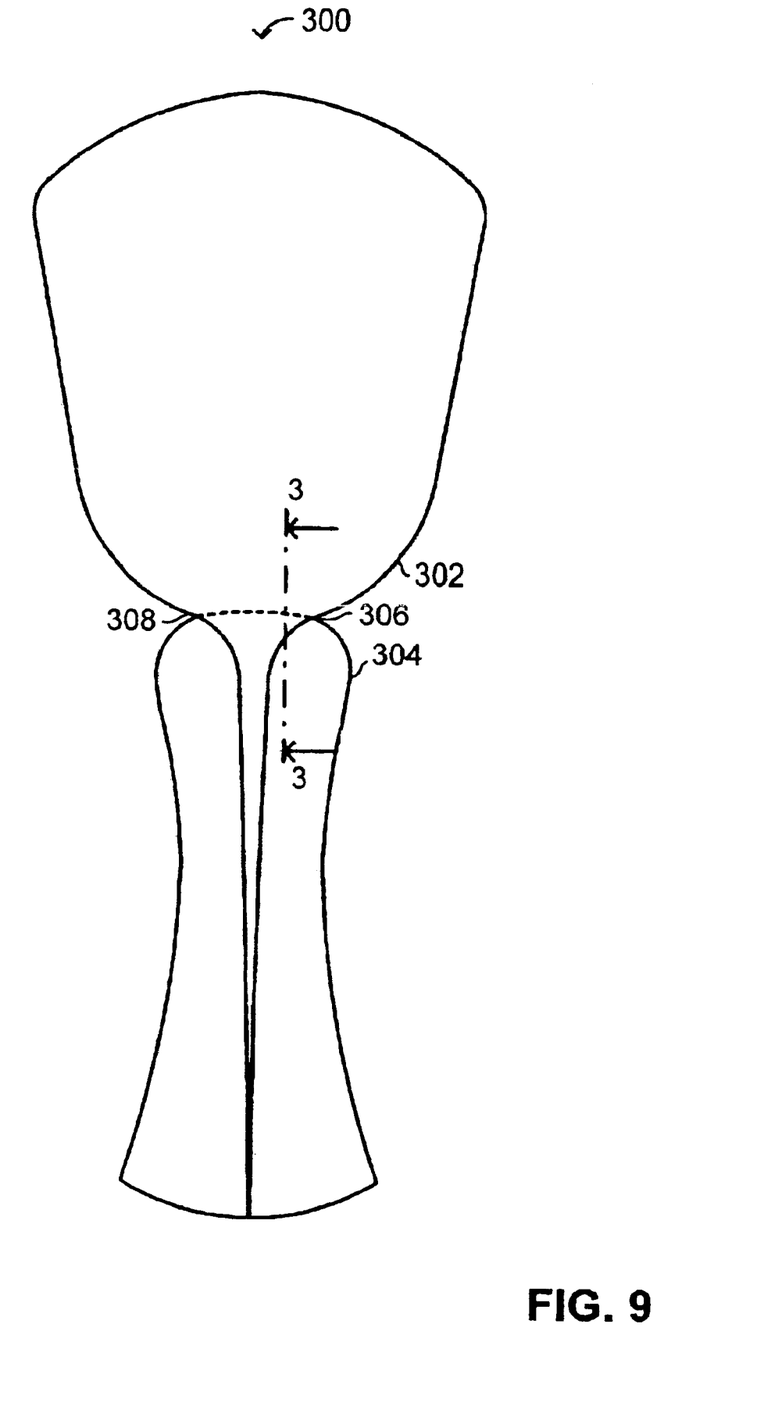
FIG. 9 is a schematic plan view of a pad, constructed and operative in accordance with a further preferred embodiment of the present invention.
Figure 10:
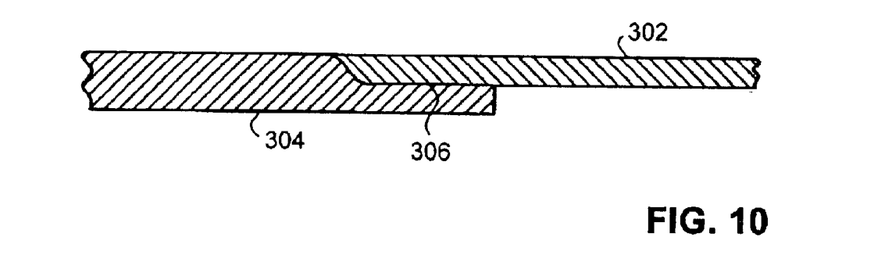
FIG. 10 is a cross-sectional enlarged view of the pad of FIG. 9, taken along broken line 3 in FIG. 9.

Reference is now made to FIGS. 9 and 10. FIG. 9 is a schematic plan view of a pad, generally referenced 300, constructed and operative in accordance with another preferred embodiment of the present invention. Pad 300 is shown while viewing from direction of a user. FIG. 10 is a cross-sectional enlarged view of the pad of FIG. 9, taken along broken line 3 in FIG. 9.

The upper part of the sides or side-flaps of narrow portion 304 of pad 300 overlap under the lower part of wide portion 302 of pad 300, in regions 306 and 308. The overlaps at regions 306 and 308 thus reduce the probability of leakage of fluids from pad 50 of FIG. 5, and contamination of crotch of the undergarment 88, but still provide for the bending of wide portion 302 toward directions opposed to the bending direction of narrow portion 304.

It will be appreciated by persons skilled in the art that the present invention is not limited to what has been particularly shown and described hereinabove. Rather the scope of the present invention is defined only by the claims, which follow.

What is claimed is:

1. A sanitary pad comprising:

a wide portion;

a narrow portion connected to said wide portion, defining two lateral notches dividing between said wide portion and said narrow portion; and at least two fold lines preformed on said narrow portion, said at least two fold lines inwardly emanating from said two lateral notches and curving downwardly away from said wide portion and toward the longitudinal median of said narrow portion.

2. A sanitary pad as in claim 1, wherein said at least two fold lines are preformed on an upper surface of said narrow portion.

3. A sanitary pad as in claim 1, wherein said at least two fold lines are preformed on a lower surface of said narrow portion.

4. A sanitary pad as in claim 1, wherein said at least two fold lines are preformed by methods of the following list or any combination thereof:

mechanically pressing the pad along the curves of a desired fold line;

joining an constituents thereof chemically;

applying heat;

applying a laser beam;

applying an adhesive; and applying mechanical vibrations.

5. A sanitary pad as in claim 1, wherein part of a thickness of the sanitary pad is joined there between to create said at least tow fold lines.

6. A sanitary pad as in claim 1, wherein an entire thickness thereof is joined there between to create said at least two fold lines.

7. A sanitary pad as in claim 1, wherein a thick fold strip is formed along and on any part of said narrow portion between said at least two fold lines.

8. A sanitary pad as in claim 1, wherein said at least two fold lines comprise a lower pair of fold lines preformed on the lower surface of said narrow portion and an upper pair of fold lines preformed on the upper surface of said narrow portion.

9. A sanitary pad as in claim 8, wherein a thick fold strip is preformed between said upper pair of fold lines and said lower pair of fold lines.

10. A sanitary pad as in claim 1, further comprising a traverse fold line preformed across said wide portion between said notches.

11. A sanitary pad as in claim 10, wherein said traverse fold line comprises an arcuate fold line.

12. A sanitary pad as in claim 11, wherein said arcuate fold line comprises a convex curve toward said wide portion.

13. A sanitary pad as in claim 10, wherein said traverse fold line is preformed on an upper surface of said pad.

14. A sanitary pad as in claim 10, wherein part of a thickness of the pad is joined there between to create said traverse fold line.

15. A sanitary pad as in claim 10, wherein an entire thickness thereof is joined there between to create said traverse fold line.

16. A sanitary pad as in claim 10, wherein a thick fold strip is formed along said traverse fold line.

17. A sanitary pad as in claim 1, wherein a contour of said wide portion and a contour of said narrow portion converge at said notches, said contour of said wide portion emanates laterally from said notches and curves to flare toward an upper part of said wide portion, said contour of the narrow portion emanates laterally from said notches and curves to flare toward a lower part of said narrow portion.

18. A sanitary pad as in claim 1, wherein contour lines of said wide portion and said narrow portion converge at said notches, and each of said at least two fold lines emanate from said notches in an uninterrupted curve continuing said contour lines of said wide portion and said narrow portion.

19. A sanitary pad as in claim 1, wherein said at least two fold lines converge at a convergence point located on a longitudinal median of said narrow portion.

20. A sanitary pad as in claim 19, wherein said at least two fold lines extend along at least a substantial part of said narrow portion.

21. A sanitary pad as in claim 1, further comprising a stabilizing bonding rim along contour edges of said narrow portion and said wide portion.

22. A sanitary pad as in claim 21, wherein said stabilizing bonding is provided by a method or any combination of methods, from the list consisting of:

mechanically pressing;

joining constituents thereof chemically;

applying heat;

applying a laser beam;

applying an adhesive; and applying mechanical vibration.

23. A sanitary pad as in claim 1, wherein said at least two fold lines comprise dashed lines.

24. A sanitary pad as in claim 1, wherein the upper part of sides of said narrow portion overlap under the lower part of sides of said wide portion.

25. A sanitary pad as in claim 1, comprising an absorbent layer, a transmitting layer, a backing sheet, and a peel away sheet, and wherein adhesive layers are interleaved between said backing sheet and said peel away sheet.

26. A sanitary pad as in claim 25, wherein said absorbent layer comprises a plurality of substantially parallel laminates manufactured from a fluid absorbing material.

27. A sanitary pad as in claim 26, wherein said fluid absorbing material comprises any of the following constituents or a combination thereof:

plastic fibers;

cotton fibers; and wood pulp fibers.

28. A sanitary pad as in claim 25, wherein said transmitting layer covers an entire upper surface of the pad.

29. A sanitary pad as in claim 25, wherein said transmitting layer is substantially thinner than said absorbent layer.

30. A sanitary pad as in claim 25, wherein said transmitting layer is constructed from a cellulose material.

31. A sanitary pad as in claim 25, wherein said adhesive layers are manufactured from an adhesive which detachably adheres to undergarments.

32. A sanitary pad as in claim 31, wherein the adhesive of said adhesive layers is substantially inert to the human body.

33. A sanitary pad as in claim 25, wherein said peel away sheet is detachable from said adhesive layers without damaging the form or substance of said adhesive layers.

34. A sanitary pad as in claim 33, wherein said peel away sheet comprises a foil.

* * * * *